US006309596B1

(12) United States Patent
Xia et al.

(10) Patent No.: US 6,309,596 B1
(45) Date of Patent: Oct. 30, 2001

(54) TREATMENT OF CONTACT LENSES WITH AQUEOUS SOLUTION COMPRISING A BIGUANIDE DISINFECTANT STABILIZED BY A POLOXAMINE

(75) Inventors: Erning Xia, Penfield; David J. Heiler, Avon, both of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/211,547

(22) Filed: Dec. 15, 1998

(51) Int. Cl.[7] ................. A01N 2/08; A61L 2/00
(52) U.S. Cl. .................... 422/28; 422/1; 422/5; 422/28; 422/29; 424/94.1
(58) Field of Search ............... 134/30; 422/28, 422/1, 5, 29; 424/94.1

(56) References Cited

U.S. PATENT DOCUMENTS

| 4,758,595 | * | 7/1988 | Ogunbiyi et al. | 514/635 |
|---|---|---|---|---|
| 4,820,352 | * | 4/1989 | Riehammer | 134/30 |
| 4,886,658 | * | 12/1989 | Charbonneau | 424/53 |
| 5,326,552 | * | 7/1994 | Na et al. | 424/4 |
| 5,356,555 | * | 10/1994 | Huth et al. | 252/106 |
| 5,422,073 | * | 6/1995 | Mowery-McKee et al. | 422/28 |
| 5,453,435 | * | 9/1995 | Raheja et al. | 514/402 |
| 5,593,636 | * | 1/1997 | Mowery-McKee et al. | 422/28 |
| 5,593,637 | | 1/1997 | Mowrey-McKee et al. | 422/28 |
| 5,604,189 | | 2/1997 | Zhang et al. | 510/112 |
| 5,718,895 | * | 2/1998 | Asgharian | 424/94.1 |
| 5,817,277 | * | 10/1998 | Mowery-McKee et al. | 422/28 |

| 6,051,645 | * | 4/2000 | Suzuki et al. | 524/500 |

FOREIGN PATENT DOCUMENTS

| WO 86 02001A | * | 10/1986 | (EP) . |
|---|---|---|---|
| WO 97 28827A | * | 8/1997 | (EP) . |
| WO 97 43373A | * | 11/1997 | (EP) . |
| WO 98 20738A | * | 5/1998 | (EP) . |
| WO 99 24542A | * | 5/1999 | (EP) . |

* cited by examiner

Primary Examiner—Robert J. Warden, Sr.
Assistant Examiner—Imad Soubra
(74) Attorney, Agent, or Firm—Robert B. Furr, Jr.; Denis A. Polyn

(57) ABSTRACT

The present invention is directed to a biguanide-containing disinfecting solution containing a particular type of poloxamine for stabilizing a polymeric biguanide. The poloxamine surfactant comprises at least about 90 weight percent of poly(oxyethylene) and poly(oxypropylene) segments, in one or more copolymer chains, wherein the weight average molecular weight of said surfactant is from about 10,000 to about 30,000 and wherein at least about 70 weight percent of said poly(oxyethylene) and poly(oxypropylene) segments are poly(oxyethylene) segments, and wherein the HLB value is at least 27. The method of the present invention comprises cleaning and disinfecting a contact lens with the above-described solution. Products according to the present invention provide enhanced cleaning while maintaining biocidal efficacy.

15 Claims, No Drawings

TREATMENT OF CONTACT LENSES WITH AQUEOUS SOLUTION COMPRISING A BIGUANIDE DISINFECTANT STABILIZED BY A POLOXAMINE

FIELD OF THE INVENTION

The present invention is directed toward a method for treating contact lenses and compositions for the same. The subject invention includes the use of an aqueous biguanide-containing disinfecting solution including an improved surfactant system comprising a poloxamine that improves the stability of a polymeric biguanide disinfectant. Preferred embodiments of the invention include methods and compositions for simultaneously cleaning and disinfecting contact lenses.

BACKGROUND OF THE INVENTION

Generally, contact lenses in wide use fall into three categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, and (3) gel, hydrogel or soft type lenses. The hard and rigid-type lenses, because they are characterized by low vapor diffusion and absorb only minor amounts of aqueous fluids, have a lower tendency to bind ingredients used in contact-lens care solutions. On the other hand, soft lenses have a greater tendency to bind active ingredients in contact-lens solutions and, therefore, it is especially challenging to develop solutions designed for the treatment of soft-type lenses, whether made from the more traditional copolymers of 2-hydroxyethylene methacrylate (HEMA) or from the newer silicon-containing hydrogel materials.

After wear, contact lenses must be disinfected to kill harmful microorganisms that may be present or grow on the lenses. Some of the most popular products for disinfecting lenses are multi-purpose solutions that can be used to clean, disinfect and wet contact lenses, followed by direct insertion (placement on the eye) without rinsing. Obviously, the ability to use a single solution for contact-lens care is an advantage. Such a solution, however, must be particularly gentle to the eye, since at least some of the solution will be on the lens when inserted and will come into contact with the eye.

U.S. Pat. No. 4,758,595 to Ogunbiyi et al. disclosed that a contact-lens solution containing a polyaminopropyl biguanide (PAPB), also known as polyhexamethylene biguanide (PHMB), has advantageous properties for a multi-purpose solution, especially in the presence of a borate buffer. These disinfecting and preservative solutions are especially noteworthy for their broad spectrum of bactericidal and fungicidal activity at low concentrations coupled with very low toxicity when used with soft-type contact lenses. Compositions containing PHMB and borate have been commercialized in various products including multi-purpose solutions, at relatively low levels of about 1 ppm or less, for use with soft contact lenses. U.S. Pat. No. 4,820,352 to Riedhammer discloses the use of poloxamine surfactants in general as cleaning agents in combination with biguanide disinfectants. U.S. Pat. Nos. 5,817,277; 5,593,637; and 5,422,073 to Mowrey-McKee et al. disclose a multi-purpose solution comprising a polyhexamethylene biguanide (PHMB) disinfectant in combination with the surfactants tyloxapol, poloxamine, or poloxamer for cleaning and disinfecting contact lenses.

A significant challenge to improving the cleaning efficacy of a multi-purpose solution is to simultaneously improve or maintain its disinfecting efficacy. The addition of more effective cleaning agents sometimes has the effect of reducing the efficacy of the disinfecting agent, in particular reducing the stability of the disinfecting agent over time. In particular, it is known that polymeric biguanides are not completely stable over time, hence requiring a limited shelf life when used at relatively low concentrations that are preferred for comfort reasons. Another challenge has been to develop a formula that is, on the one hand, maximally efficacious and, on the other hand, sufficiently gentle to be not only safe, but also comfortable for in-the-eye use.

One type of product that would require more efficacious cleaning and disinfection is a multi-purpose solution that would not require digital rubbing of the contact lens with the solution as part of its regimen of use. With conventional contact-lens cleaners or disinfectants, including multi-purpose solutions, lens wearers typically need to digitally or manually rub the contact lenses (typically between a finger and palm or between fingers) during treatment of the contact lenses. The necessity for the daily "rubbing" of contact lenses adds to the time and effort involved in the daily care of contact lenses. Many contact-lens wearers dislike having to perform such a regimen or consider it to be inconvenient. Some wearers may be negligent in the proper "rubbing" regimen, which may result in contact-lens discomfort and other problems. Sometimes rubbing, if performed too rigorously, which is particularly apt to occur with beginning lens wearers, may damage the lenses. This can be especially problematic when a replacement lens is not immediately available.

Contact lens solutions that qualify as a "Chemical Disinfecting Solution" do not require rubbing to meet biocidal performance criteria (for destroying representative bacteria and fungi) set by the U.S. Food and Drug Administration (FDA) under the Premarket Notification (510 k) Guidance Document For Contact Lens Care Products, May 1, 1997. In contrast, a contact-lens solution, referred to as a "Chemical Disinfecting System," not qualifying as a Chemical Disinfecting Solution, requires a rubbing regimen to pass biocidal performance criteria. Traditionally, multi-purpose solutions (used for disinfecting and wetting or for disinfecting, cleaning, and wetting) have qualified as a Chemical Disinfecting System, but not as a Chemical Disinfecting Solution.

Traditional contact-lens multi-purpose solutions may depend on a rubbing regimen, not only for efficacious disinfection, but also for efficacious cleaning. Thus, in order to develop a contact-lens care solution that would not require rubbing, both improved or stronger cleaning and disinfection may be needed, while at the same time maintaining the solution sufficiently gentle for in-the-eye use.

Thus, it would be desirable to obtain a multi-purpose contact-lens solution that would provide increased disinfecting efficacy, particularly over time. Further, it would be desirable to obtain improved cleaning efficacy while maintaining or increasing the biocidal efficacy of the product without adversely affecting the comfort or safety in terms of the level of toxicity to eye tissue. While still more challenging to develop, it would also be desirable to develop a multi-purpose solution that exhibits both efficacious cleaning and disinfection of a contact lens, without requiring a rubbing regimen, or at least not inherently or invariably requiring it for acceptable performance, which multi-purpose solution allows direct placement of the contact lens on the eye following soaking

SUMMARY OF THE INVENTION

The present invention is directed to a biguanide-containing disinfecting solution containing a specially selected class of poloxamines for stabilizing polymeric biguanides, which combination of ingredients is especially advantageous for contact lens solutions that provide enhanced disinfecting and/or enhanced cleaning efficacy. The present invention includes methods for treating contact lenses and compositions used for the same. Specifically, the present invention involves contacting a lens with an aqueous solution having a pH of 5 to 8 and comprising:

(a) an effective amount of at least one polymeric biguanide germicide;

(b) an effective amount of a poloxamine surfactant comprising at least about 90 weight percent of poly(oxyethylene) and poly(oxypropylene) segments, in one or more copolymer chains, wherein the weight average molecular weight of said surfactant is from about 10,000 to about 30,000 and wherein at least about 70 weight percent of said poly(oxyethylene) and poly(oxypropylene) segments are poly(oxyethylene) segments, and wherein the HLB value is at least 27.

Preferably, the composition also comprises an effective amount of one or more sequestering agents. The method of the present invention comprises cleaning and disinfecting a contact lens with the above-described solution. In the preferred embodiment, products according to the present invention also provide enhanced cleaning while maintaining or improving biocidal efficacy. In another embodiment of the present invention, the subject lens-care solution can both disinfect and clean a contact lens, meeting desired performance criteria, within a regimen not involving or requiring digital rubbing or the like. As such, the present invention offers significant advantages, including greater convenience and safety, compared to traditional cleaning and disinfecting solutions and methods of use.

DETAILED DESCRIPTION OF THE INVENTION

The present invention can be used with all contact lenses such as conventional hard, soft, rigid and soft gas permeable, and silicone (including both hydrogel and non-hydrogel) lenses, but is especially useful for soft lenses. By the term "soft lens" is meant a lens having a proportion of hydrophilic repeat units such that the water content of the lens during use is at least 20% by weight. The term "soft contact lens" as used herein generally refers to those contact lenses that readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. However, newer soft lenses, especially for extended wear, are being made from high-Dk silicone-containing materials.

The present invention is useful for contact-lens care solutions for simultaneously disinfecting and cleaning contact lenses, especially those that also qualify as a multi-purpose solution. In order to disinfect, the solution must contain one or more active ingredients (for example, antimicrobial agents and/or preservatives) in sufficient concentrations to destroy harmful microorganisms on the surface of a contact lens within the recommended minimum soaking time. The recommended minimum soaking time is included in the package instructions for use of the solution. The term "disinfecting solution" does not exclude the possibility that the solution may also be useful as a preserving solution, or that the disinfecting solution may be useful for other purposes such as daily cleaning, rinsing and storage of contact lenses, depending on the particular formulation.

A multi-purpose solution is useful for cleaning, disinfecting, storing, and rinsing a contact lens, particularly soft contact lenses. Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more cleaning agents in sufficient concentrations to loosen and remove loosely held lens deposits and other contaminants on the surface of a contact lens, which may be used in conjunction with digital manipulation (for example, manual rubbing of the lens with a solution) or with an accessory device that agitates the solution in contact with the lens, for example, a mechanical cleaning aid. The critical micelle concentration of a surfactant-containing solution is one way to evaluate its cleaning effectiveness.

Traditionally, multi-purpose solutions on the market have required a regimen involving mechanical rubbing of the contact lens with the multi-purpose solution, in order to provide the required disinfection and cleaning. Such a regimen is required under governmental regulatory authorities (for example, the FDA or Food & Drug Administration in the USA) for a Chemical Disinfection System that does not qualify as a Chemical Disinfecting Solution. In one embodiment of the present invention, it is possible to formulate a cleaning and disinfecting product that, on the one hand, is gentle enough to be used as a wetting agent and, on the other hand, is able to provide improved cleaning and disinfection in the absence of a rubbing regimen. For example, a product qualifying as a Chemical Disinfecting Solution must meet biocidal performance criteria established by the U.S. FDA for Contact Lens Care Products (May 1, 1997) which criteria does not involve rubbing of the lenses. In one embodiment of the present invention, a composition is formulated to meet the requirements of the FDA or ISO Stand-Alone Procedure for contact lens disinfecting products. Similarly, compositions of the present invention can be formulated to provide enhanced cleaning without the use of a rubbing regimen. Such formulations may ensure higher patient compliance and greater universal appeal than traditional multi-purpose disinfecting and cleaning products.

The solutions according to the present invention are physiologically compatible. Specifically, the solution must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO (International Standards Organization) standards and U.S. FDA (Food & Drug Administration) regulations. The solution should be sterile in that the absence of microbial contaminants in the product prior to release must be statistically demonstrated to the degree necessary for such products.

The subject solution includes at least one polymeric biguanide antimicrobial agent. A polymeric biguanide can optionally be combined with a non-polymeric biguanide.

Representative non-polymeric biguanides are the bis (biguanides), such as alexidine or chlorhexidine or salts thereof. Representative polymeric biguanides include hexamethylene biguanide (PHMB). Preferred polymeric biguanides, and water-soluble salts thereof, have the following formula:

(IV)

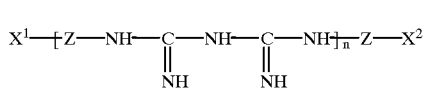

wherein Z is an organic divalent bridging group which may be the same or different throughout the polymer, n is on average at least 3, preferably on average 5 to 20, and $X^1$ and $X^2$ are independently selected from the groups —$NH_2$ and

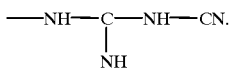

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Zeneca (Wilmington, Del.) under the trademark Cosmocil™ CQ. Such polymers and water-soluble salts are referred to polyhexamethylene biguanide (PHMB) or polyaminopropyl biguanide (PAPB). The term polyhexamethylene biguanide, as used herein, is meant to encompass one or more biguanides have the following formula:

(V)

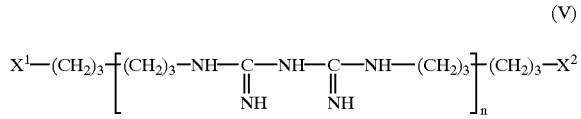

wherein $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated herein by reference. Preferably, the water-soluble salts are compounds where n has an average value of 2 to 15, most preferably 3 to 12.

A disinfecting amount of antimicrobial agent is an amount that will at least partially reduce the microorganism population in the formulations employed. Preferably, a disinfecting amount is that which will reduce the microbial burden of representative bacteria by two log orders in four hours and more preferably by one log order in one hour. Most preferably, a disinfecting amount is an amount which will eliminate the microbial burden on a contact lens when used according to its regimen for the recommended soaking time (FDA Chemical Disinfection Efficacy Test—July, 1985 Contact Lens Solution Draft Guidelines). Typically, such agents are present in concentrations ranging from about 0.00001 to about 0.5% (w/v), and more preferably, from about 0.00003 to about 0.5% (w/v).

In one preferred embodiment, a polymeric biguanide is used in combination with a bis(biguanide) compound. Polymeric biguanides, in combination with bis(biguanide)s such as alexidine, are effective in concentrations as low as 0.00001 weight percent (0.1 ppm). It has also been found that the bactericidal activity of the solutions may be enhanced or the spectrum of activity broadened through the use of a combination of such polymeric biguanides with alexidine or similar biguanide, as disclosed in commonly assigned copending U.S. application Ser. No. 60/065501, filed Nov. 12, 1997, hereby incorporated by reference.

An optional non-biguanide disinfectant/germicide can be employed as a solution preservative, but it may also function to potentiate, complement or broaden the spectrum of microbiocidal activity of another germicide. This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to, quaternary ammonium polymers, sorbic acid, alkyl triethanolamines, and mixtures thereof. Representative examples of the polymeric quaternary ammonium salts used in ophthalmic applications are poly[(dimethyliminio)-2-butene-1,4-diyl chloride], [4-tris(2-hydroxyethyl) ammonio]-2-butenyl-w-[tris(2-hydroxyethyl)ammonio]dichloride (chemical registry number 75345-27-6) generally available as polyquaternium 1® from ONYX Corporation. Novel Polyquaterniums are disclosed in copending U.S. application Ser. No. 60/065510 filed Nov. 12, 1997, hereby incorporated by reference.

The acid-addition salts of the germicides used in the present composition may be derived from an inorganic or organic acid. In most circumstances it is preferable that the salts be derived from an acid which is readily water soluble and which affords an anion that is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids. The hydrochloride salt is preferred.

As indicated above, the present solution comprises at least one poloxamine surfactant that provides improved stability and disinfecting efficacy over time. In general, poloxamine surfactants comprise a poly(oxypropylene)-poly (oxyethylene) adduct of ethylene diamine. The poloxamine is suitably employed in amounts ranging from 0.01 to 10.0 percent, preferably 0.1 to 5.0 percent, most preferably 0.5 to 1.5 percent by weight of the composition or solution. The surfactant should be soluble in the lens care solution, not become turbid, and should be non-irritating to eye tissues. The poloxamines required by the present invention comprise at least about 90 weight percent of poly(oxyethylene) and poly(oxypropylene) segments, preferably at least 95 to 100 weight percent of poly(oxyethylene) and poly (oxypropylene) segments in one or more block copolymer chains, wherein the weight average molecular weight of said surfactant is from about 4000 to about 30,000 and wherein at least about 70 percent of said segments are poly (oxyethylene) segments. The poloxamine should have an HLB (hydrophilic/lipophilic balance) value of at least 27. Such surfactants are commercially available from BASF Performance Chemicals (Mount Olive, N.J.) under their registered trademark "Tetronic." Poloxamine is the CTFA Cosmetic Ingredient Dictionary's adopted name for this group of surfactants.

The HLB of a surfactant is known to be a major factor in determining the emulsification characteristics of a nonionic surfactant. In general, surfactants with lower HLB values are more lipophilic, while surfactants with higher HLB values are more hydrophilic. The HLB values of various poloxamines are provided by BASF Performance Chemicals in published commercial literature.

In accordance with the present invention, it has been surprisingly found that the HLB value of the poloxamine affects the stability and hence microbiocidal efficacy of polymeric biguanides over time. Without wishing to be bound by theory, one possible theory that may account for the observed increased stability of biguanides in the presence of poloxamines having an HLB of at least 27 is that such poloxamines may have a decreased tendency to bind to the walls of the plastic container, typically a polyalkylene-containing material, such as HDPE (high density polyethylene), and this in turn may prevent or decrease the tendency of the biguanide to also bind to the walls of the container where it may be more prone to decomposition over time due to a closer proximity to heat and/or light.

Optionally, additional surfactants can be included in the present composition, either amphoteric, cationic, anionic, or nonionic which may be present (individually or in combination) in amounts up to 10 percent, preferably up to 5 percent weight by volume (w/v) of the total composition (solution). Preferably, any additional surfactants are amphoteric or nonionic surfactants, which when used impart cleaning and conditioning properties. The surfactant should be soluble in the lens care solution and non-irritating to eye tissues. Optionally additional non-ionic surfactants include polyethylene glycol esters of fatty acids, e.g. coconut, polysorbate, polyoxyethylene or polyoxypropylene ethers of higher alkanes ($C_{12}$–$C_{18}$). Examples include polysorbate 20 (available under the trademark Tween® 20), polyoxyethylene (23) lauryl ether (Brij® 35), polyoxyethyene (40) stearate (Myrj® 52), polyoxyethylene (25) propylene glycol stearate (Atlas® G 2612). One preferred surfactanct is tyloxopal, as disclosed in commonly assigned copending U.S. application Ser. No. 09/211,748, filed Dec. 15, 1998, filed on even date herewith and hereby incorporated by reference.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

Various other surfactants suitable for in the invention can be readily ascertained, in view of the foregoing description, from *McCutcheon's Detergents and Emulsifiers,* North American Edition, McCutcheon Division, MC Publishing Co., Glen Rock, N.J. 07452 and the *CTFA International Cosmetic Ingredient Handbook,* Published by The Cosmetic, Toiletry, and Fragrance Association, Washington, D.C.

As indicated above, the concentration of the surfactant, either the required poloxamine alone or the required poloxamine in combination with additional conventional surfactants, is suitably in total from 0.01 to 10.0 percent weight by volume (w/v), preferably 0.1 to 5.0 percent, and most preferably 0.5 to 1.5 percent.

In one preferred embodiment, it has been found that the cleaning efficacy of the solution can be enhanced by including a carbonate or bicarbonate salt in the amount of 0.010 to 1.0 percent by weight of the total composition (solution), preferably 0.05 to 0.2 weight percent, most preferably 0.08 to 0.12 weight percent. Suitably, the carbonate or bicarbonate salt is an alkali metal salt, including, for example, sodium bicarbonate, sodium carbonate, potassium carbonate, potassium bicarbonate, and mixtures thereof. The most preferred carbonates are sodium carbonate and sodium bicarbonate.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose, povidone, polyvinyl alcohol, and the like. Such viscosity builders may be employed in amounts ranging from about 0.01 to about 4.0 weight percent or less.

In the present application, the amount of the germicide or other components or ingredients in solution according to the present invention refers to the amount formulated and introduced into the solution at the time the solution is made.

In addition to a biguanide germicide and the stabilizing amount of poloxamine, the solutions of the present invention include a buffering system. In a preferred embodiment, the buffer system includes at least one phosphate buffer and at least one borate buffer, which buffering system has a buffering capacity of 0.01 to 0.5 mM, preferably 0.03 to 0.45, of 0.01 N of HCl and 0.01 to 0.3, preferably 0.025 to 0.25, of 0.01 N of NaOH to change the pH one unit. Buffering capacity is measured by a solution of the buffers only.

The pH of the present solutions should be maintained within the range of 5.0 to 8.0, more preferably about 6.0 to 8.0, most preferably about 6.5 to 7.8. By the terms "buffer" or "buffer substance" is meant a compound that, usually in combination with at least one other compound, provides a buffering system in solution that exhibits buffering capacity, that is, the capacity to neutralize, within limits, either acids or bases (alkali) with relatively little or no change in the original pH. The term "buffering capacity" is defined to mean the millimoles (mM) of strong acid or base (or respectively, hydrogen or hydroxide ions) required to change the pH by one unit when added to one liter (a standard unit) of the buffer solution. From this definition, it is apparent that the smaller the pH change in a solution caused by the addition of a specified quantity of acid or alkali, the greater the buffer capacity of the solution. See, for example, *Remington: The Science and Practice of Pharmacy,* Mack Publishing Co., Easton, Pa. (19th Edition 1995), Chapter 17, pages 225–227. The buffer capacity will depend on the kind and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Phosphate buffers include, for example, phosphoric acid and its salts, for example, phosphate buffers (including combinations of $M_2HPO_4$, $MH_2PO_4$ and $MH_2PO_4$, wherein M is independently an alkali metal salt such as K and Na). The term phosphate includes compounds that produces phosphoric acid or its salt in solution. As will be readily appreciated by the skilled artisan, buffering systems include but are not limited to the combination of a weak acid and the salt of the weak acid (the so-called conjugate base).

An especially preferred buffer system is the combination of boric acid and mono and/or dibasic phosphate salt such as sodium and/or disodium phosphate. An alternate buffer system, for example, are the combination of sodium borate and phosphoric acid or the combination of sodium borate and the monobasic phosphate.

Suitably the solution comprises about 0.05 to 2.5% by weight of a phosphoric acid or its salt and 0.1 to 5.0% by weight of boric acid or its salt. The phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

Other buffer substance may optionally be used in the composition. For example, traditionally known buffers include, for example, citrates, citric acid, sodium bicarbonate, TRIS, and the like. Other ingredients in the solution, while having other functions, may also affect the buffer capacity. For example, EDTA, often used as a sequestrant, may have a noticeable effect on the buffer capacity of a composition. Generally, buffers will be used in amounts ranging from about 0.05 to 2.5 percent by weight, and preferably, from 0.1 to 1.5 percent.

Borate buffers are known for enhancing the efficacy of certain polymeric biguanides. For example, U.S. Pat. No. 4,758,595 to Ogunbiyi et al. discloses that a contact-lens solution containing a polyaminopropyl biguanide (PAPB), also known as polyhexamethylene biguanide (PHMB), has enhanced efficacy when combined with a borate buffer. Applicants have found that borate buffers also enhance the efficacy of biguanides in general, including bis(biguanides) such as alexidine.

In addition to buffering agents, in some instances it may be desirable to include sequestering agents in the present solutions in order to bind metal ions which might otherwise react with the lens and/or protein deposits and collect on the lens. They are usually added in amounts ranging from about 0.01 to about 0.2 weight percent.

Examples include Ethylene-diaminetetraacetic acid (EDTA) and its salts (disodium), gluconic acid, citric acid, tartaric acid and their salts, e.g. sodium salts. Preferred sequestering agents, which are also effective for removing protein deposits, are the phosphonate compounds represented by the following Formula (I):

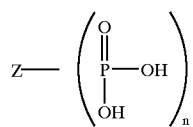

(I)

wherein Z is a connecting radical equal in valence to n, wherein n is an integer from 1 to 6, preferably 1 to 3. Such phosphonate compounds are disclosed in WO 97/31659. The subject aqueous solution suitably includes at least 0.003 percent weight by volume of the subject phosphonic compound in the total solution, preferably 0.005 to 2.5 percent weight by volume and more preferably about 0.01 to 0.5 percent weight by volume in the total solution.

Typically, the aqueous solutions of the present invention for treating contact lenses are also adjusted with tonicity agents, to approximate the osmotic pressure of normal lachrymal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation. Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 450 mOsm/kg and more preferably between about 250 to about 350 mOsm/kg, and most preferably between about 280 to about 320 mOsm/kg.

Preferably, the invention is formulated as a "multipurpose solution," meaning that the solution may be used for cleaning, chemical disinfection, storing, and rinsing a contact lens. A multi-purpose solution preferably has a viscosity of less than 75 cps, preferably 1 to 50 cps, and most preferably 1 to 25 cps and is preferably is at least 95 percent weight by volume water in the total composition.

As stated above, contact lenses are cleaned and disinfected by contacting the lens with the subject aqueous solution. Although this may be accomplished by simply soaking a lens in the subject solution, greater cleaning can be achieved if a few drops of the solution are initially placed on each side of the lens, and the lens is rubbed for a period of time, for example, approximately 20 seconds. The lens can then be subsequently immersed within several milliliters of the subject solution. Preferably, the lens is permitted to soak in the solution for at least four hours. Furthermore, the lens is preferably rinsed with fresh solution after any rubbing step and again after being immersed within the solution. The lenses are then removed from the solution, rinsed with the same or a different solution, for example a preserved isotonic saline solution and then replaced on the eye.

The aqueous solutions of the present invention are especially useful for soft contact lenses, with or without further additives. Nevertheless, the solutions of the present invention may be formulated into specific contact lens care products, such as wetting solutions, soaking solutions, cleaning and conditioning solutions, as well as multipurpose type lens care solutions, etc. and mixtures thereof. Finally, such solutions can be applied to the lenses outside the eye or while on the eye, for example, in the form of droplets.

As indicated above, contact-lens wearers are commonly required to digitally or manually rub the contact lenses (typically between a finger and palm or between fingers) during daily cleaning and/or disinfecting of contact lenses. In one embodiment of the present invention, a method is provided in which rubbing is not required during treatment with the claimed specified solution, between removal from the eye and replacement of the lens following lens care. In a preferred embodiment of such a method, a soft lens is disinfected or both disinfected and cleaned with a multipurpose solution or an effective multi-purpose solution that is the only daily solution needed for treating the lens outside the eye. Thus, in one embodiment of a method according to the invention, the described solution is used to treat a contact lens without rubbing, by a method comprising:

(a) soaking the contact lens that has not been rubbed with the solution for a specified time period, and (b) direct placement of the treated contact lens on the eye of the wearer.

Typically, step (a) may involve immersing the contact lens in the solution. Soaking may optionally comprise shaking or similarly agitating a container of the solution by manual means. Preferably, step (a) involves a period of soaking the contact lens in a container wherein the contact lens is completely immersed in the solution. By the term "direct placement" is herein meant that the solution is not diluted or rinsed off the lens with a different contact-lens solution prior to "insertion" or placement on the eye. In a particularly preferred embodiment, the method uses a product that is formulated as a multi-purpose, wherein no other solution or product is required for daily cleaning of the lens, with the possible exception of an enzyme cleaner.

In yet another embodiment of a method according to the present invention, the claimed solution is used to clean a frequent replacement lens (FRL) or planned replacement lens (PRL) that is planned for replacement after not more than about three months of use in the eye, or that is planned for replacement after not more than about 30 days of use in the eye, or that is planned for replacement after not more than about two weeks in the eye. Preferably, the lens is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate.

As an illustration of the present invention, several examples are provided below. These examples serve only to further illustrate aspects of the invention and should not be construed as limiting the invention.

EXAMPLE 1

An example of a preferred formulation of the subject invention is provided below in Table 1.

TABLE 1

| Constituent | mg/g | % W/W |
| --- | --- | --- |
| Polyhexamethylene biguanide HCl (as a 20% w/w solution available under the mark Cosmocil ® CQ, from ICI Chemical Co.) | 0.0008 | 0.00008 |
| Alexidine | 0.002 | 0.0002 |
| Boric Acid | 8.30 | 0.830 |
| Sodium Phosphate (dibasic anhydrous) | 3.10 | 0.310 |
| Sodium Phosphate (monobasic, anhydrous) | 1.55 | 0.155 |
| Sodium Chloride | 3.75 | 0.375 |
| Poloxamine (Tetronic ® 908 from BASF Co.) | 10.00 | 1.000 |
| Tetrasodium phosphonate (as a 30% (w/w) solution available under the mark DeQuest ® 2016 from Monsanto Co.) | 1.000 | 0.100 |
| Sodium Carbonate | 1.00 | 0.100 |
| Sodium Hydroxide, 1N and/or Hydrochloric Acid | as required for pH adjustment | as required for pH adjustment |
| Purified Water | | Balance to 100 |

This solution was prepared by weighing out the necessary amount of the ingredients, including sodium carbonate, the tetrasodium salt of 1-hydroxyethylidene-1,1-diphosphonic acid (also referred to as tetrasodium etidronate), commercially available as DeQuest® 2016 from Monsanto (St. Louis, Mo.) into a glass beaker. The solution is prepared by gradually heating 80 percent of the water to 80° C. while dissolving the phosphonate and the buffer substances. The sodium chloride is then added to the solution and dissolved, followed by the addition of surfactant. After the solution is cooled to room temperature, the alexidine, PHMB, and carbonate in solution are added through a sterile filter. The pH of the resulting solution was between about 7.3 to 7.5. (If necessary, the pH of the solution may be adjusted by use of an appropriate amount of hydrochloric acid or sodium hydroxide, as indicated in Table 1).

EXAMPLE 2

This Example illustrates that the microbiocidal efficacy of a solution according to the present invention employing a poloxamine with an HLB value of at least compared to various solutions employing a poloxamine with an HLB of less than 27. The poloxamine Tetronic 908 has an HLB value of 31, whereas (for comparison) Tetronic 1108 exhibits an HLB value of 24. The antimicrobial efficacy of each of various compositions for the chemical disinfection of contact lenses was evaluated. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231), and *Fusarium solani* (ATCC 36031). The test organisms were cultured on appropriate agar and the cultures were harvested using sterile DPBST (Dulbecco's Phosphate Buffered Saline plus 0.05% w/v polysorbate 80) or a suitable diluent and transferred to a suitable vessel. Spore suspensions were filtered through sterile glass wool to remove hyphal fragments. *Serratia marcescens,* as appropriate, was filtered (eg., through a $1.2\mu$ filter) to clarify the suspension. After harvesting, the suspension was centrifuged at no more than 5000×g for a maximum of 30 minutes at 20–25° C. The supernatant was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1 \times 10^7 – 10^8$ cfu/mL. The appropriate cell concentration may be estimated by measuring the turbidity of the suspension, for example using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1.0 \times 10^5 – 10^6$ cfu/mL, the volume of the inoculum not exceeding 1% of the sample volume. Dispersion of the inoculum was ensured by vortexing the sample for at least 15 seconds. The inoculated product was stored at 10–25° C. Aliquots in the amount of 1.0 mL were taken of the inoculated product for determination of viable counts after certain time periods of disinfection. The time points for the bacteria were, for example, 1, 2, 3, and 4 hours when the proposed regimen soaking time was 4 hours. Yeast and mold were tested at an additional timepoint of $\geq 16$ hours (4 times the regimen time). The suspension was mixed well by vortexing vigorously for at least 5 second. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of trypticase soy (TSA) agar for bacteria and Sabouraud dextrose agar (SDA) for mold and yeast. The bacterial recovery plates were incubated at 30–35° C. for 2–4 days. The yeast was incubated at 20–30° C. for 2–4 days and mold recovery plates at 20–25° C. for 3–7 days. The average number of colony forming units was determined on countable plates. Countable plates refer to 30–300 cfu/plates for bacteria and yeast, and 8 to 80 cfu/plate for mold except when colonies are observed only for the $10^0$ or $10^{-1}$ dilution plates. The microbial reduction was then calculated at the specified time points. In order to demonstrate the suitability of the medium used for growth of the test organisms and to provide an estimation of the initial inoculum concentration, inoculum controls were made by dispersing an identical aliquot of the inoculum into a suitable diluent, for example DPBST, using the same volume of diluent used to suspend the organism as listed above. Following inoculation in a validated neutralizing broth and incubation for an appropriate period of time, the inoculum control must be between $1.0 \times 10^5 - 1.0 \times 10^6$ cfu/mL The solutions were evaluated based on the performance requirement referred to as the "Stand-Alone Procedure for Disinfecting Products" (hereafter the "stand-alone test") and is based on the Disinfection Efficacy Testing for contact lens care products under the Premarket Notification (510(k)) Guidance Document For Contact Lens Care Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995). The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time.

A formulation according to Example 1 (Formulation A) comprising Tetronic® 908 poloxamine was tested and compared to the same solution except replacing the Tetronic® 908 poloxamine with Tetronic® 1107 poloxamine (Comparative Formulation B). A summary of the stability (biocidal efficacy) results of the two formulations are provided in Table 2 below, each at 40° C. after three months.

TABLE 2

| PRODUCT | HOURS | Form. A With Tetronic 908 Poloxamine At 40° C. | Comparative Form. B With Tetronic 1107 Poloxamine at 40° C. |
|---|---|---|---|
| Staphylococcus Aureus | 1 Hour | 3.9 | 2.5 |
|  | 2 Hours | >4.6 | 4.1 |
|  | 3 Hours | >4.6 | 3.9 |
|  | 4 Hours | 4.0 | >4.6 |
| Pseudomonas Aeruginosa | 1 Hour | 3.6 | 3.3 |
|  | 2 Hours | >4.6 | >4.6 |
|  | 3 Hours | >4.6 | >4.6 |
|  | 4 Hours | >4.6 | >4.6 |
| Serratia marcescens | 1 Hour | 3.7 | 2.5 |
|  | 2 Hours | 4.7 | 4.4 |
|  | 3 Hours | >4.7 | >4.7 |
|  | 4 Hours | >4.7 | >4.7 |
| Candida Albicansi | 1 Hour | 2.1 | 0.9 |
|  | 2 Hours | 3.5 | 1.1 |
|  | 3 Hours | 4.0 | 1.5 |
|  | 4 Hours | 4.6 | 16 |
|  | 24 Hours | >4.7 | 3.3 |
| Fusarium solani | 1 Hour | 1.0 | 0.3 |
|  | 2 Hours | 1.2 | 0.3 |
|  | 3 Hours | 1.7 | 0.2 |
|  | 4 Hours | 1.8 | 0.2 |
|  | 24 Hours | 4.3 | 0.9 |
| TEST DISPOSITION |  | PASS | FAIL |

These results show that the microbicidal efficacy of the biguanide disinfecting system, when in combination with Tetronic® 908 poloxamine, is more stable when compared to the microbicidal efficacy of the solutions with Tetronic® 1107 poloxamine. (The former poloxamine has an HLB value of 31, whereas the latter poloxamine has an HLB value of 24). It is believed that the comparatively less microbicidal efficacy of comparative formulations B is due to instability of the formulation in view of the enhanced cleaning agents. Confirming this belief, additional tests were conducted employing UV analysis to determine the concentration of the PHMB in each formulation at the end of the various time periods following initial formulation, as summarized in Table 3 below. This results showed that over time, the amount of PHMB in Formula A decreased less than the amount of PHMB in Comparative Formula B.

TABLE 3

Summary of Stability Test Results of PHMB at a Target Conc. of 0.8 ppm

| Formulations | Zero Month | One Month | Two Month | Three Month |
|---|---|---|---|---|
| Comp. Form. B |  |  |  |  |
| 25° C. | 0.690 | 0.635 (Pass) | 0.5941 (Pass) | 0.59 |
| 40° C. | 0.690 | 0.503 (Pass) | 0.474 (Fail) | 0.44 |
| Form. A |  |  |  |  |
| 25 C | 0.660 | 0.663 (Pass) | 0.481 (Pass) | 0.56 |
| 40° C. | 0.660 | 0.599 (Pass) | 0.519 (Pass) | 0.57 |

It can be seen that the Formula with Tetronic 908 having the higher HLB value resulted in increased stability for the PHMB biguanide.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

What is claimed is:

1. A method of disinfecting and cleaning a soft contact lens with a multi-purpose solution, which method comprises:
   (a) soaking the lens in an ophthalmically safe solution, such that acceptable disinfection of the contact lens is obtained within a minimum recommended soaking period, the solution having a pH of 5 to 8 and comprising, in formulation, the following components:
      (i) an effective amount of at least one polymeric biguanide germicide, and (ii) an effective amount of a poloxamine surfactant comprising at least about 90 weight percent of poly(oxyethylene) and poly(oxypropylene) segments, in one or more copolymer chains, wherein the weight average molecular weight of said surfactant is from about 10,000 to about 30,000 and wherein at least about 70 weight percent of said poly(oxyethylene) and poly(oxypropylene) segments are poly(oxyethylene) segments, and wherein the HLB value is 27–37, and (b) directly placing the treated lens on the eye of the wearer, such that (i) rinsing with a different solution prior to placement on the eye is not required, and (ii) no other solution is required for daily cleaning of the lens.

2. The method of claim 1 comprising the sequential steps of rubbing the lens with the solution, followed by immersing the lens within the solution.

3. The method of claim 1 wherein the method provides complete cleaning of the lens such that digital rubbing of the lens is not necessary to clean or disinfect the lens.

4. The method of claim 1 wherein the solution further comprises a bis(biguanide) or salt thereof.

5. The method of claim 1 wherein the solution has a pH from about 6 to about 8 and an osmolality of between about 250 to 350 mOsm/kg.

6. The method of claim 1 in which the buffering system comprises a phosphoric acid and/or a salt thereof, and boric acid and/or a salt thereof.

7. The method of claim 1 further comprising 0.01 to 1.0 percent by weight of an alkali metal carbonate or bicarbonate.

8. An aqueous solution having a pH from about 5 to about 8 for treating contact lenses, comprising:

(a) an effective amount of at least one polymeric biguanide germicide, and (b) an effective amount of a poloxamine surfactant comprising at least about 90 weight percent of poly(oxyethylene) and poly(oxypropylene) segments, in one or more copolymer chains, wherein the weight average molecular weight of said surfactant is from about 10,000 to about 30,000 and wherein at least about 70 weight percent of said poly(oxyethylene) and poly(oxypropylene) segments are poly(oxyethylene) segments, and wherein the HLB value is 27–31.

9. The solution of claim 8 further comprising a bis(biguanide) or salt thereof.

10. The solution of claim 8 wherein the solution has a pH from about 6 to about 8 and an osmolality of between about 250 to 350 mOsm/Kg.

11. The solution of claim 8 in which the buffering system comprises a phosphoric acid and/or a salt thereof, and boric acid and/or a salt thereof.

12. The solution of claim 8 further comprising 0.01 to 1.0 percent by weight of an alkali metal carbonate or bicarbonate.

13. The method of claim 1 wherein said polymeric biguanide germicide comprises polyhexamethylene biguanide.

14. The method of claim 1 wherein the germicide further comprises a bis(biguanide).

15. The method of claim 14 wherein the bis(biguanide) is alexidine.

* * * * *